US012569169B2

(12) United States Patent (10) Patent No.: US 12,569,169 B2
Huang et al. (45) Date of Patent: Mar. 10, 2026

(54) NON-INVASIVE FLEXIBLE BLOOD GLUCOSE DETECTING AND SLEEP MONITORING DEVICE

(71) Applicant: Taiwan-Asia Semiconductor Corporation, Hsinchu City (TW)

(72) Inventors: Hsiu-Jung Huang, Hsinchu City (TW); Sheng-Wei Chen, Hsinchu City (TW)

(73) Assignee: TAIWAN-ASIA SEMICONDUCTOR CORPORATION, Hsinchu City (TW)

( * ) Notice: Subject to any disclaimer, the term of this patent is extended or adjusted under 35 U.S.C. 154(b) by 337 days.

(21) Appl. No.: 18/490,602

(22) Filed: Oct. 19, 2023

(65) Prior Publication Data

US 2024/0138718 A1 May 2, 2024

(30) Foreign Application Priority Data

Nov. 2, 2022 (TW) .................................. 111141907

(51) Int. Cl.
| A61B 5/1455 | (2006.01) |
| A61B 5/00 | (2006.01) |
| A61B 5/145 | (2006.01) |

(52) U.S. Cl.
CPC ........ *A61B 5/14532* (2013.01); *A61B 5/1455* (2013.01); *A61B 5/4809* (2013.01);
(Continued)

(58) Field of Classification Search
CPC . A61B 5/14532; A61B 5/1455; A61B 5/4809; A61B 5/6801; A61B 5/4806;
(Continued)

(56) References Cited

U.S. PATENT DOCUMENTS

| 10,357,201 B2 | 7/2019 | Rogers et al. | |
| 2007/0093698 A1* | 4/2007 | Goldberger | .......... A61B 5/6833 |
| | | | 600/310 |

(Continued)

FOREIGN PATENT DOCUMENTS

| CN | 112020327 A | 12/2020 |
| WO | WO03050643 A2 | 6/2003 |

*Primary Examiner* — Ankit D Tejani
*Assistant Examiner* — Joshua Brendon Solomon
(74) *Attorney, Agent, or Firm* — MUNCY, GEISSLER, OLDS & LOWE, P.C.

(57) ABSTRACT

The present invention provides a non-invasive flexible blood glucose detecting and sleep monitoring device for monitoring the sleep state and blood glucose state of the detected person. The non-invasive flexible blood glucose detecting and sleep monitoring device includes a detection module including: a substrate; a plurality of optical modules, each being an optical cover plates with a coating layer; retaining walls, being disposed on the substrate, and the retaining walls respectively establishing a first space and a second space with the substrate and the optical modules; a light emitting unit, being disposed in the first space; and the sensing unit, being disposed in the second space. The non-invasive flexible blood glucose detecting and sleep monitoring device further includes a flexible piezoelectric module for being placed on the detected person; and a detecting unit, being connected to the detection module and the flexible piezoelectric module.

10 Claims, 7 Drawing Sheets

(52) U.S. Cl.
CPC .... *A61B 5/6801* (2013.01); *A61B 2560/0406*
(2013.01); *A61B 2560/0462* (2013.01); *A61B*
*2562/0238* (2013.01); *A61B 2562/0247*
(2013.01); *A61B 2562/063* (2013.01); *A61B*
*2562/146* (2013.01)

(58) Field of Classification Search
CPC .... A61B 2560/0406; A61B 2560/0462; A61B
2562/0238; A61B 2562/0247; A61B
2562/063; A61B 2562/146; A61B
2562/06; A61B 2562/16; A61B 2562/164
See application file for complete search history.

(56) References Cited

U.S. PATENT DOCUMENTS

2016/0192842 A1 * 7/2016 Inagaki ............... A61B 5/0059
600/476
2020/0060584 A1 2/2020 Musin
2021/0038092 A1 2/2021 Amin et al.
2021/0338158 A1 11/2021 Kendall et al.

* cited by examiner

351

311

NON-INVASIVE FLEXIBLE BLOOD GLUCOSE DETECTING AND SLEEP MONITORING DEVICE

CROSS-REFERENCES TO RELATED APPLICATIONS

This application claims priority to Taiwan Patent Application No. 111141907 filed on Nov. 2, 2022, which is hereby incorporated by reference in its entirety.

BACKGROUND OF THE INVENTION

Field of the Invention

The present invention is applied to the field of sleep monitoring and blood glucose detecting in biomedical technology, in particular a non-invasive flexible blood glucose detecting and sleep monitoring device for monitoring the sleep state and blood glucose state of a detected person.

Descriptions of the Related Art

Traditionally, flexible piezoelectric film devices are primarily used in sleep monitoring devices, and rarely have multiple functions such as non-invasive blood glucose detection.

A sleep monitoring device disclosed in U.S. Patent Publication No. US20210038092A1 includes a layered sensor including at least one substrate layer with a plurality of laterally adjacent substrates. The substrate layer may be formed by interdigitating fingers of a first sheet with fingers of a second sheet. Combining multiple substrates in a single layer of a layered sensor may allow multiple materials and/or sensing mechanisms to be combined in a single layer. However, the layered sensor only has the capability of sleep monitoring without the capability of non-invasive observing body conditions such as blood glucose monitoring.

In view of this, the present invention provides a non-invasive flexible blood glucose detecting and sleep monitoring device, which changes the design of the outermost layer of the prior art by alternately adding an array of blind holes or random blind holes in the protective layer and the adhesive layer above the electrode layer to embed the non-invasive blood glucose detection module therein. Accordingly, it has a broadened scope of use compared with the prior art.

SUMMARY OF THE INVENTION

The primary objective of the present invention is to provide a non-invasive flexible blood glucose detecting and sleep monitoring device for monitoring the sleep state and blood glucose state of a detected person.

In order to achieve the above objective or other objectives, the present invention provides a non-invasive flexible blood glucose detecting and sleep monitoring device, which is used to monitor the sleep state and blood glucose state of the detected person. The non-invasive flexible blood glucose detecting and sleep monitoring device includes a detection module, a flexible piezoelectric module and a detecting unit. The detection module includes a substrate; a plurality of optical modules, each being an optical cover plate with a coating layer; retaining walls disposed on the substrate, the retaining walls respectively establishing a first space and a second space with the substrate and the optical modules; a light emitting unit disposed in the first space, the light emitting unit generating a first light and emitting the first light in a direction toward the detected person; a sensing unit disposed in the second space, the sensing unit receiving a second light from the detected person, and the sensing unit generating a corresponding first signal according to the second light, wherein the second light is a reflective light of the first light. The flexible piezoelectric module is used for being placed on the detected person. The flexible piezoelectric module includes a first protective layer formed with a first blind hole for the detection module to be disposed in; a first electrode layer electrically connected to the substrate and receiving the first signal; a second electrode layer; a first piezoelectric layer disposed between a side of the first electrode layer and a side of the second electrode layer, the first piezoelectric layer inducing a piezoelectric effect therein to generate a second signal between the first electrode layer and the second electrode layer after bearing an external applied force; and a second protective layer disposed on the other side of the second electrode layer. The detecting unit is connected to the detection module and the flexible piezoelectric module, and the detecting unit receives the first signal and the second signal.

Furthermore, the flexible piezoelectric module further includes a supporting layer, and a side of the supporting layer is disposed on a side of the second electrode layer.

Furthermore, the flexible piezoelectric module further includes a ground layer disposed on the other side of the supporting layer.

Furthermore, the flexible piezoelectric module further includes an adhesive layer selectively disposed on a side of the first protective layer, a side of the second protective layer, a side of the second electrode layer, a side of the supporting layer and a side of the ground layer.

Furthermore, the flexible piezoelectric module further includes a third electrode layer, a fourth electrode layer and a second piezoelectric layer. The third electrode layer is disposed on the other side of the supporting layer. The fourth electrode layer is disposed on a side of the second protective layer. The second piezoelectric layer induces a piezoelectric effect therein to generate a third signal between the third electrode layer and the fourth electrode layer after bearing the external applied force, and the third signal is transmitted to the detecting unit.

Furthermore, the second protective layer is further formed with a second blind hole for an additional detection module to be disposed in.

Furthermore, a substrate of the additional detection module is electrically connected to the fourth electrode layer.

Furthermore, a plurality of the second blind holes are provided and a plurality of the additional detection modules are provided. The number of the plurality of the second blind holes is not less than the number of the plurality of the additional detection modules.

Furthermore, a plurality of the first blind holes are provided and a plurality of the additional detection modules are provided, and the number of the plurality of the first blind holes is not less than the number of the plurality of the additional detection modules.

Furthermore, an arrangement of the first blind holes and the second blind holes is a regular arrangement or an arbitrary arrangement.

Compared with the prior art, the present invention provides a non-invasive flexible blood glucose detecting and sleep monitoring device, which not only collects and analyzes the sleep state of the detected person, but also detects changes in blood glucose during sleep, and its flexibility increases its ease of use.

DETAILED DESCRIPTION OF THE PREFERRED EMBODIMENT

In order to fully understand the objectives, features and effects of the present invention, the present invention will be described in detail through the following specific embodiments and accompanying drawings as follows.

In the present invention, "a" or "an" is used to describe one or more units, devices and components described herein. Such a descriptive term is merely for the convenience of illustration and to provide a general sense of the scope of the present invention. Therefore, unless expressly stated otherwise, the term "a" or "an" is to be understood to include one or at least one, and the singular form also includes the plural form.

As used herein, the term "comprise" "include," "have," "contain" or any other similar term is not intended to exclude additional, unrecited elements. For example, a device, structure, article, or apparatus that contains a plurality of elements is not limited to those elements listed herein, but may include other elements that are not explicitly listed but are generally inherent in the device, structure, article, or apparatus. In addition, unless expressly stated to the contrary, the term "or" is meant to be an inclusive "or" and not an exclusive "or."

Figure 1A:
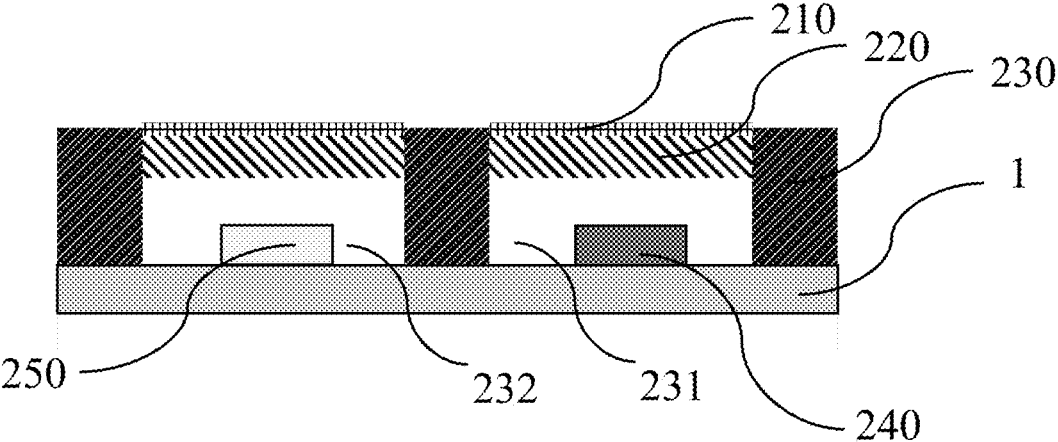
FIG. 1(a) is a layered structure diagram of the detection module of the first embodiment of the present invention.
Figure 1B:
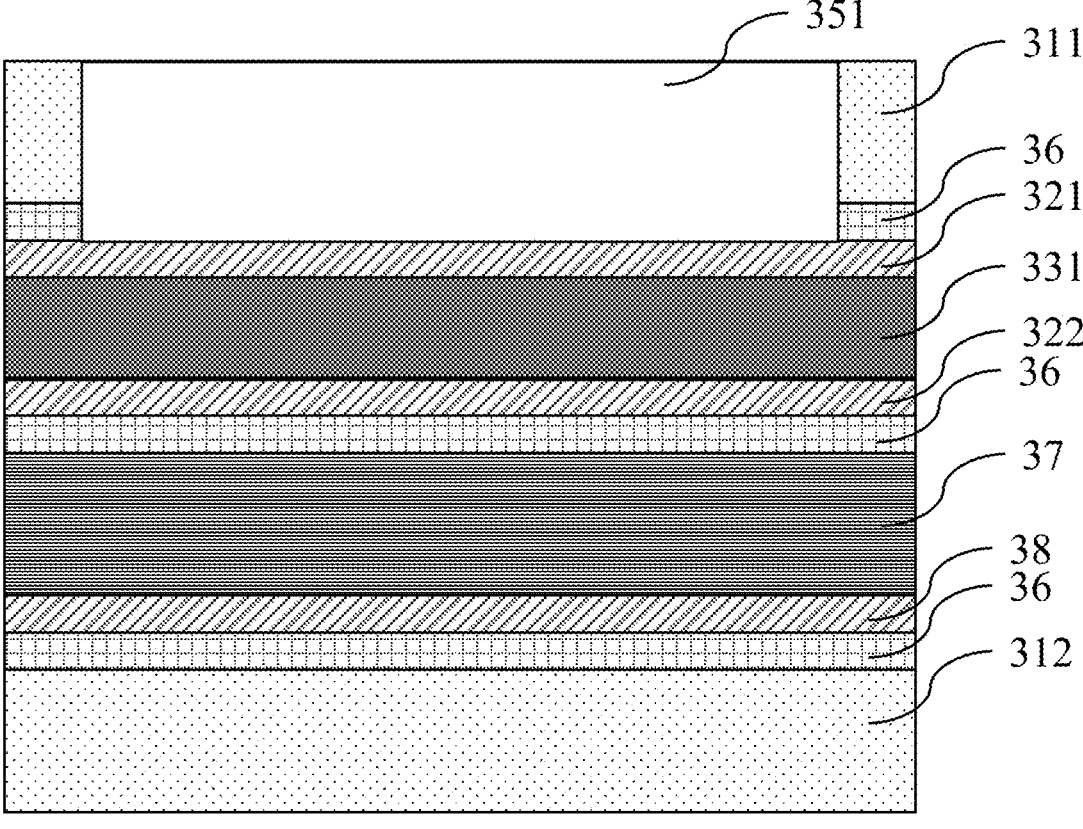
FIG. 1(b) is a layered structure diagram of the flexible piezoelectric module according to the first embodiment of the present invention.
Figure 1C:
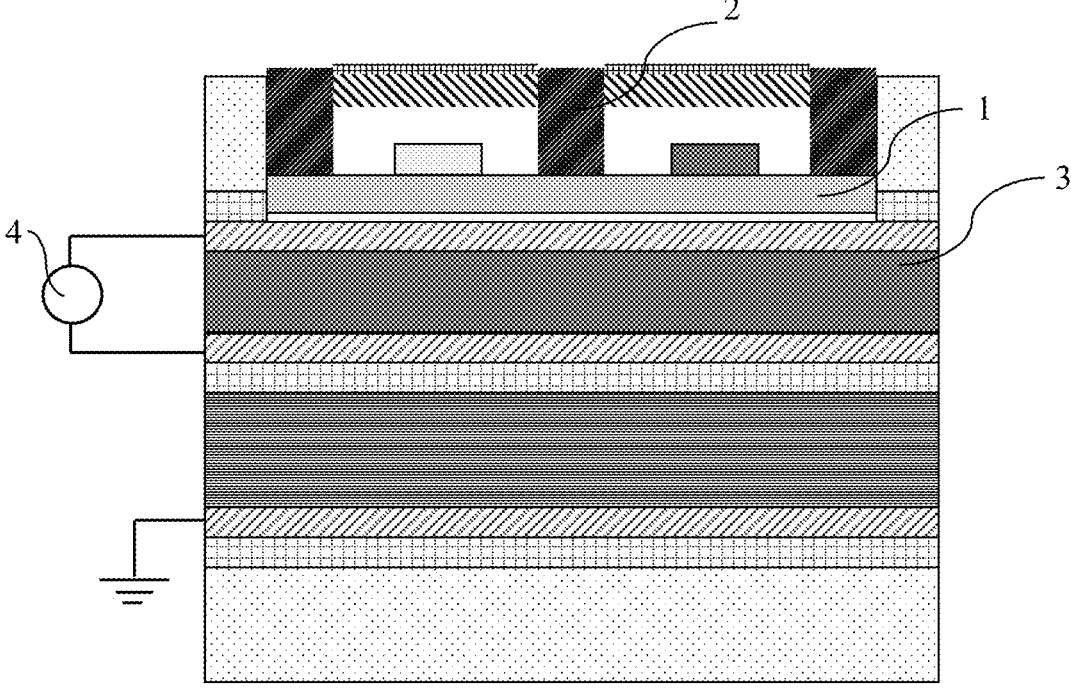
FIG. 1(c) is a layered structure diagram of the non-invasive flexible blood glucose detecting and sleep monitoring device according to the first embodiment of the present invention.

Please refer to FIG. 1(a) and FIG. 1(c), which are schematic views of the non-invasive flexible blood glucose detecting and sleep monitoring device of the first embodiment of the present invention. The non-invasive flexible blood glucose detecting and sleep monitoring device is used to monitor the sleep state and blood glucose state of a detected person. The non-invasive flexible blood glucose detecting and sleep monitoring device includes a detection module, a flexible piezoelectric module 3 and a detecting unit 4. The detection module includes a substrate 1; a plurality of optical modules 2, each being an optical cover plate 220 with a coating layer 210; retaining walls 230 disposed on the substrate 1, the retaining walls 230 respectively establishing a first space 231 and a second space 232 with the substrate 1 and the optical modules 2; a light emitting unit 240 disposed in the first space 231, the light emitting unit 240 generating a first light and emitting the first light in a direction toward the detected person; a sensing unit 250 disposed in the second space 232, the sensing unit 250 receiving a second light from the detected person, and the sensing unit 250 generating a corresponding first signal according to the second light, wherein the second light is a reflective light of the first light. The flexible piezoelectric module 3 is used for being placed on the detected person. The flexible piezoelectric module 3 includes a first protective layer 311 formed with a first blind hole 351 for the detection module to be disposed in; a first electrode layer 321 electrically connected to the substrate 1 and receiving the first signal; a second electrode layer 322; a first piezoelectric layer 331 disposed between a side of the first electrode layer 321 and a side of the second electrode layer 322, the first piezoelectric layer 331 inducing a piezoelectric effect therein to generate a second signal between the first electrode layer 321 and the second electrode layer 322 after bearing an external applied force; and a second protective layer 312 disposed on the other side of the second electrode layer 322. The detecting unit 4 is connected to the detection module and the flexible piezoelectric module 3. The detecting unit 4 receives the first signal and the second signal.

Furthermore, the flexible piezoelectric module 3 further includes a supporting layer 37, and a side of the supporting layer 37 being disposed on a side of the second electrode layer 322; a ground layer 38 disposed on the other side of the supporting layer 37; and an adhesive layer 36 selectively disposed on a side of the first protective layer 311, a side of the second protective layer 312, a side of the second electrode layer 322, a side of the supporting layer 37 and a side of the ground layer 38.

Figure 2A:
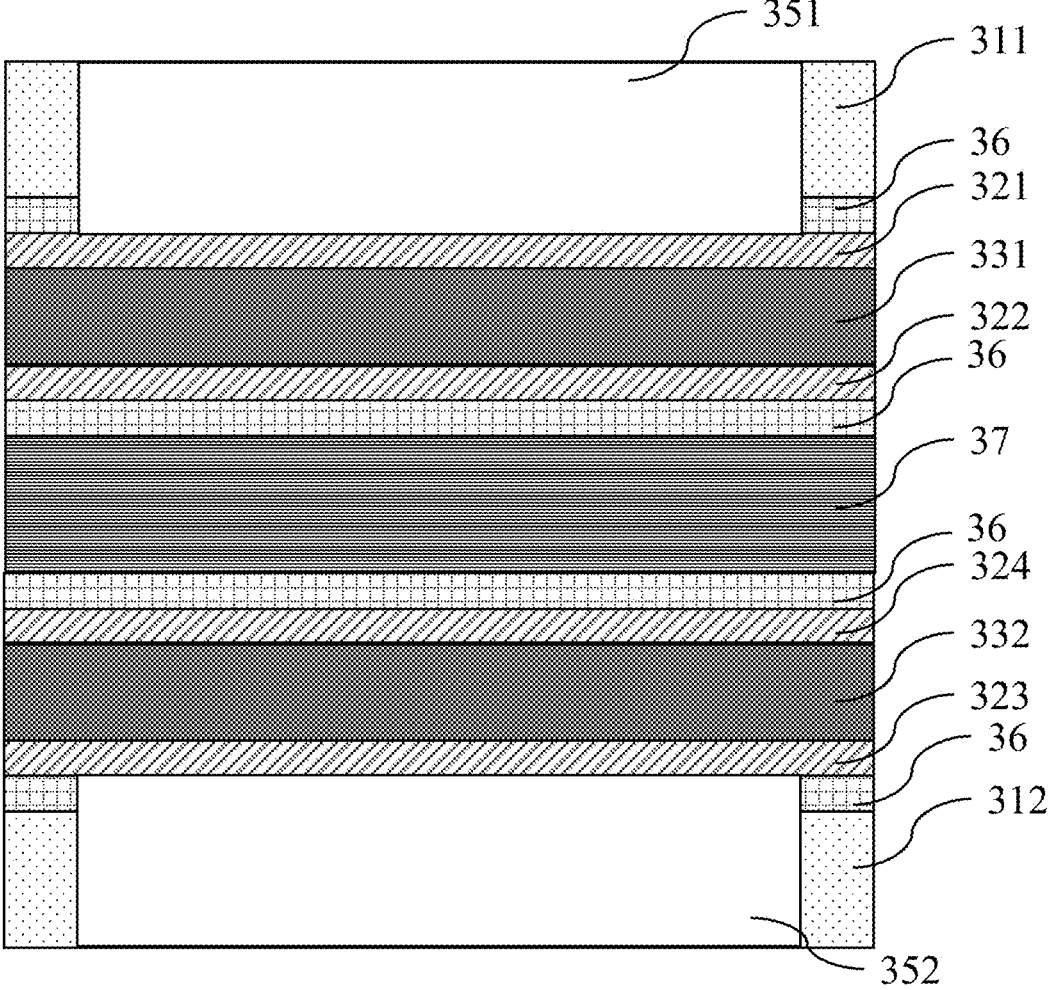
FIG. 2(a) is a layered structure diagram of the flexible piezoelectric module according to the second embodiment of the present invention.
Figure 2B:
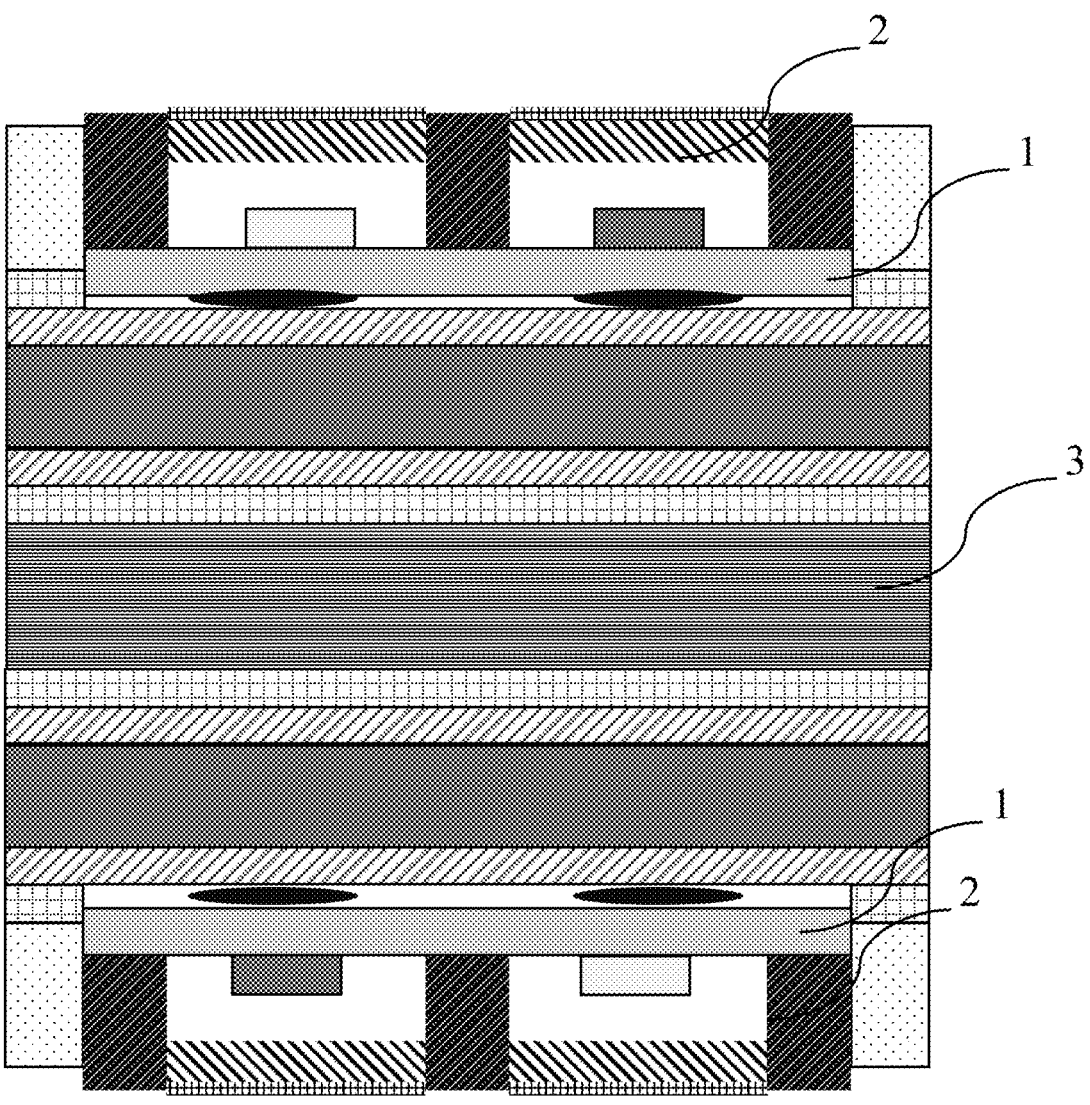
FIG. 2(b) is a layered structure diagram of a non-invasive flexible blood glucose detecting and sleep monitoring device according to the second embodiment of the present invention.

Please refer to FIG. 2(a) and FIG. 2(b), which are schematic views of the non-invasive flexible blood glucose detecting and sleep monitoring device according to the second embodiment of the present invention. The flexible piezoelectric module 3 further includes a third electrode layer 323, a fourth electrode layer 324 and a second piezoelectric layer 332. The third electrode layer 323 is disposed on the other side of the supporting layer 37. The fourth electrode layer 324 is disposed on a side of the second protective layer 312. The second piezoelectric layer 332 is disposed between the third electrode layer 323 and the fourth electrode layer 324. The second piezoelectric layer 332 induces a piezoelectric effect therein to generate a third signal between the third electrode layer 323 and the fourth electrode layer 324 after bearing the external applied force, and the third signal is transmitted to the detecting unit 4. The second protective layer 312 is further formed with a second blind hole 352 for an additional detection module to be disposed in. The substrate of the additional detection module is electrically connected to the fourth electrode layer 324.

Figure 3A:
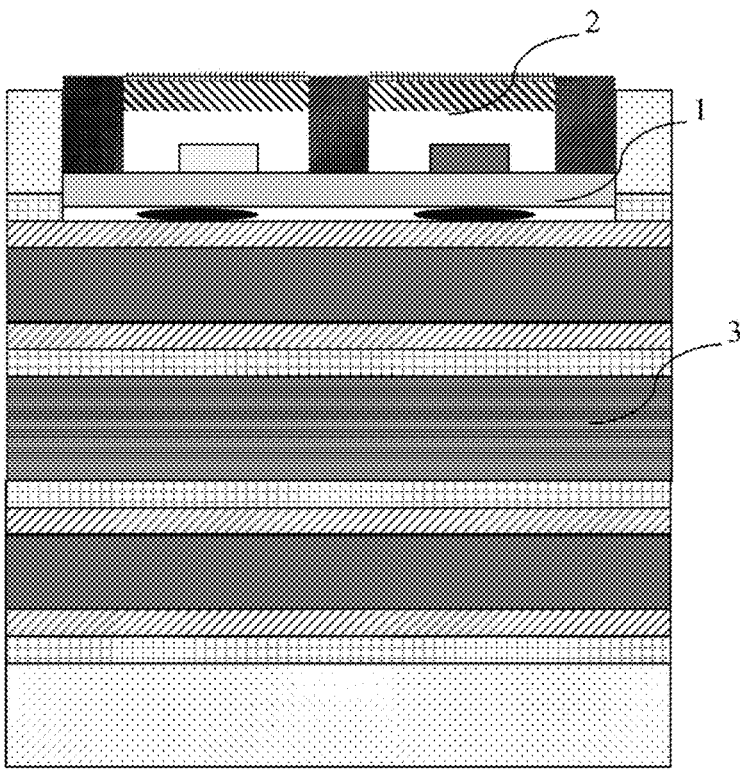
FIG. 3(a) is a layered structure diagram of a non-invasive flexible blood glucose detecting and sleep monitoring device according to the third embodiment of the present invention.
Figure 3B:
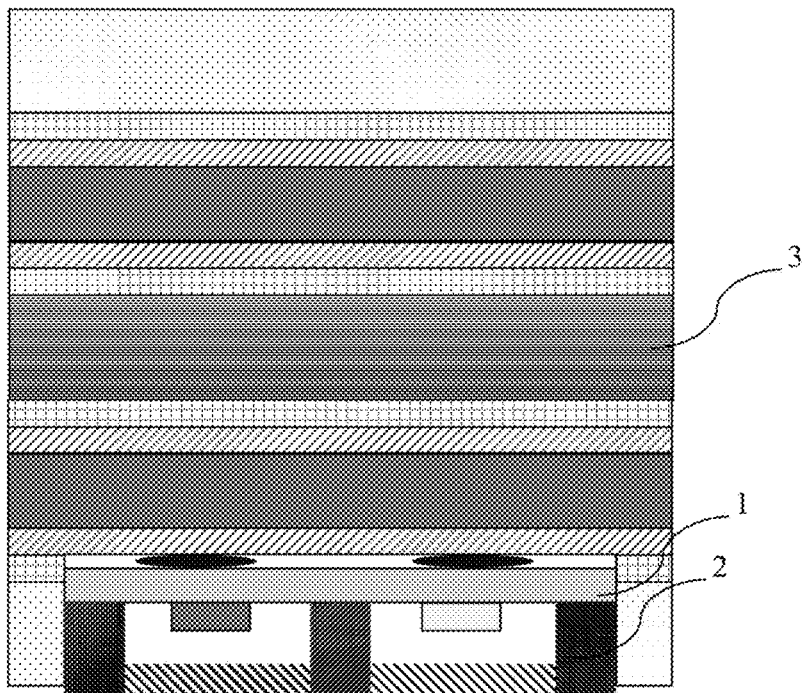
FIG. 3(b) is another layered structure diagram of the non-invasive flexible blood glucose detecting and sleep monitoring device according to the third embodiment of the present invention.

Please refer to FIG. 3(a) and FIG. 3(b), which are schematic views of the non-invasive flexible blood glucose detecting and sleep monitoring device according to the third embodiment of the present invention. FIG. 3(a) is a layered structure diagram of a non-invasive flexible blood glucose detecting and sleep monitoring device according to the third embodiment of the present invention. FIG. 3(b) is another layered structure diagram of the non-invasive flexible blood glucose detecting and sleep monitoring device according to the third embodiment of the present invention.

The flexible piezoelectric module 3 further includes a third electrode layer 323, a fourth electrode layer 324, and a second piezoelectric layer 332. The third electrode layer 323 is disposed on the other side of the supporting layer 37. The fourth electrode layer 324 is disposed on a side of the second protective layer 312. The second piezoelectric layer 332 is disposed between the third electrode layer 323 and the fourth electrode layer 324. The second piezoelectric layer 332 induces a piezoelectric effect therein to generate a third signal between the third electrode layer 323 and the fourth electrode layer 324 after bearing the external applied force, and the third signal is transmitted to the detecting unit 4. Depending on the desired orientation, the first protective layer 311 is formed with a first blind hole 351 for the detection module to be disposed in, and/or the second protective layer 312 is formed with a second blind hole 352 for the detection module to be disposed in.

Furthermore, a plurality of the second blind holes 352 are provided and a plurality of the additional detection modules are provided. The number of the plurality of the second blind holes 352 is not less than the number of the plurality of the additional detection modules. Furthermore, a plurality of the first blind holes 351 are provided and a plurality of the additional detection modules are provided, and the number of the plurality of the first blind holes 351 is not less than the number of the plurality of the additional detection modules.

Figure 4:
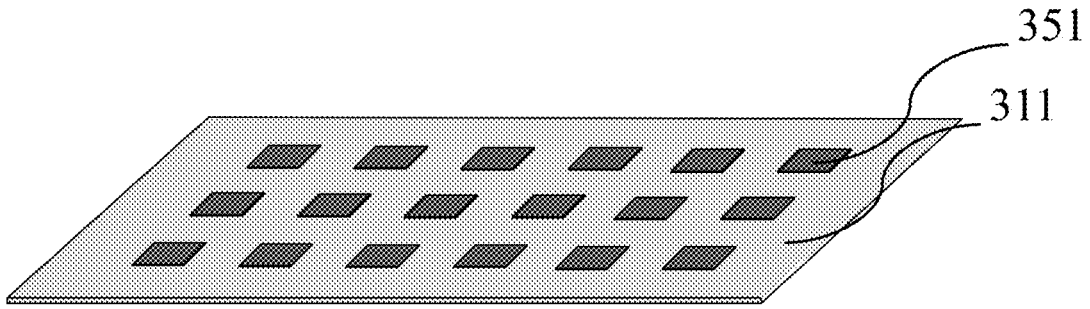
FIG. 4 is a schematic view of the arrangement of detection modules in any embodiment of the present invention.

Reference is made to FIG. 4, which is a schematic view of the arrangement of the detection modules according to an embodiment of the present invention, in which the arrangement of the first blind holes 351 and the second blind holes 352 is a regular arrangement or an arbitrary arrangement.

The present invention has been disclosed above by way of preferred embodiments; however, it should be understood by those skilled in the art that those embodiments are intended to depict the present invention only and should not be interpreted as limiting the scope of the present invention. It should be noted that any variations or alternatives equivalent to the embodiments should be included in the scope of the present invention. Therefore, the scope of the present invention should be defined by the claims of the present application.

What is claimed is:

1. A non-invasive flexible blood glucose detecting and sleep monitoring device for monitoring a sleep state and a blood glucose state of a detected person, the non-invasive flexible blood glucose detecting and sleep monitoring device comprising:
a detection module, comprising:
a substrate;
a plurality of optical modules, each being an optical cover plate with a coating layer;
retaining walls disposed on the substrate, the retaining walls respectively establishing a first space and a second space with the substrate and the optical modules;
a light emitting unit disposed in the first space, the light emitting unit generating a first light and emitting the first light in a direction toward the detected person; and
a sensing unit disposed in the second space, the sensing unit receiving a second light from the detected person, and the sensing unit generating a corresponding first signal according to the second light, wherein the second light is a reflective light of the first light;
a flexible piezoelectric module for being placed on the detected person, the flexible piezoelectric module comprising:
a first protective layer formed with a first blind hole for the detection module to be disposed in;

6 a first electrode layer electrically connected to the substrate and receiving the first signal;
a second electrode layer;
a first piezoelectric layer disposed between a side of the first electrode layer and a side of the second electrode layer, the first piezoelectric layer inducing a piezoelectric effect therein to generate a second signal between the first electrode layer and the second electrode layer after bearing an external applied force; and
a second protective layer disposed on the other side of the second electrode layer; and
a detecting unit connected to the detection module and the flexible piezoelectric module, the detecting unit receiving the first signal and the second signal.

2. The non-invasive flexible blood glucose detecting and sleep monitoring device of claim 1, wherein the flexible piezoelectric module further comprises a supporting layer, and a side of the supporting layer is disposed on a side of the second electrode layer.

3. The non-invasive flexible blood glucose detecting and sleep monitoring device of claim 2, wherein the flexible piezoelectric module further comprises a ground layer disposed on the other side of the supporting layer.

4. The non-invasive flexible blood glucose detecting and sleep monitoring device of claim 3, wherein the flexible piezoelectric module further comprises an adhesive layer selectively disposed on a side of the first protective layer, a side of the second protective layer, a side of the second electrode layer, a side of the supporting layer and a side of the ground layer.

5. The non-invasive flexible blood glucose detecting and sleep monitoring device of claim 2, wherein the flexible piezoelectric module further comprises a third electrode layer, a fourth electrode layer and a second piezoelectric layer, the third electrode layer is disposed on the other side of the supporting layer, the fourth electrode layer is disposed on a side of the second protective layer, the second piezoelectric layer induces a piezoelectric effect therein to generate a third signal between the third electrode layer and the fourth electrode layer after bearing the external applied force, and the third signal is transmitted to the detecting unit.

6. The non-invasive flexible blood glucose detecting and sleep monitoring device of claim 5, wherein the second protective layer is further formed with a second blind hole for an additional detection module to be disposed in.

7. The non-invasive flexible blood glucose detecting and sleep monitoring device of claim 6, wherein a substrate of the additional detection module is electrically connected to the fourth electrode layer.

8. The non-invasive flexible blood glucose detecting and sleep monitoring device of claim 6, wherein a plurality of the second blind holes are provided and a plurality of the additional detection modules are provided, and the number of the plurality of the second blind holes is not less than the number of the plurality of the additional detection modules.

9. The non-invasive flexible blood glucose detecting and sleep monitoring device of claim 1, wherein a plurality of the first blind holes are provided and a plurality of the additional detection modules are provided, and the number of the plurality of the first blind holes is not less than the number of the plurality of the additional detection modules.

10. The non-invasive flexible blood glucose detecting and sleep monitoring device of claim 6, wherein an arrangement of the first blind holes and the second blind holes is a regular arrangement or an arbitrary arrangement.

* * * * *